United States Patent
Lee et al.

(10) Patent No.: US 8,728,447 B2
(45) Date of Patent: *May 20, 2014

(54) TEETH-WHITENING GEL

(75) Inventors: Chih-Ta Lee, Zhongli (TW); Chun-Yi Li, Zhongli (TW); Lin-Chien Yu, Zhongli (TW); Yong-Yi Wu, Zhongli (TW)

(73) Assignee: Far Eastern New Century Corporation, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,196

(22) Filed: Jul. 18, 2012

(65) Prior Publication Data

US 2013/0216487 A1    Aug. 22, 2013

(30) Foreign Application Priority Data

Feb. 17, 2012   (TW) .............................. 101105297 A

(51) Int. Cl.
*A61K 8/64*       (2006.01)
*A61Q 11/00*    (2006.01)

(52) U.S. Cl.
USPC ............................................ 424/49; 424/401

(58) Field of Classification Search
CPC ...... A61K 8/64; A61K 2300/00; A61Q 11/00
See application file for complete search history.

(56) References Cited

U.S. PATENT DOCUMENTS

| | | |
|---|---|---|
| 4,528,180 A | 7/1985 | Schaeffer |
| 4,687,663 A | 8/1987 | Schaeffer |
| 4,849,213 A | 7/1989 | Schaeffer |
| 2004/0185013 A1 | 9/2004 | Burgio et al. |
| 2007/0086961 A1* | 4/2007 | Sagel et al. ..................... 424/53 |
| 2008/0287866 A1* | 11/2008 | Heller ............................ 604/82 |

FOREIGN PATENT DOCUMENTS

WO    WO 2005094765 A1 * 10/2005

* cited by examiner

*Primary Examiner* — Frederick Krass
*Assistant Examiner* — Tracy Liu
(74) *Attorney, Agent, or Firm* — McClure, Qualey & Rodack, LLP

(57) ABSTRACT

A teeth-whitening gel is provided. The main ingredient of the teeth-whitening gel comprises a polypeptide having halamine (N—X bond, X=Cl, Br or I) groups and a high molecular weight. By the redox properties of halamine group, the gel contacting with the teeth's surface can bleach and whiten the teeth.

8 Claims, 1 Drawing Sheet

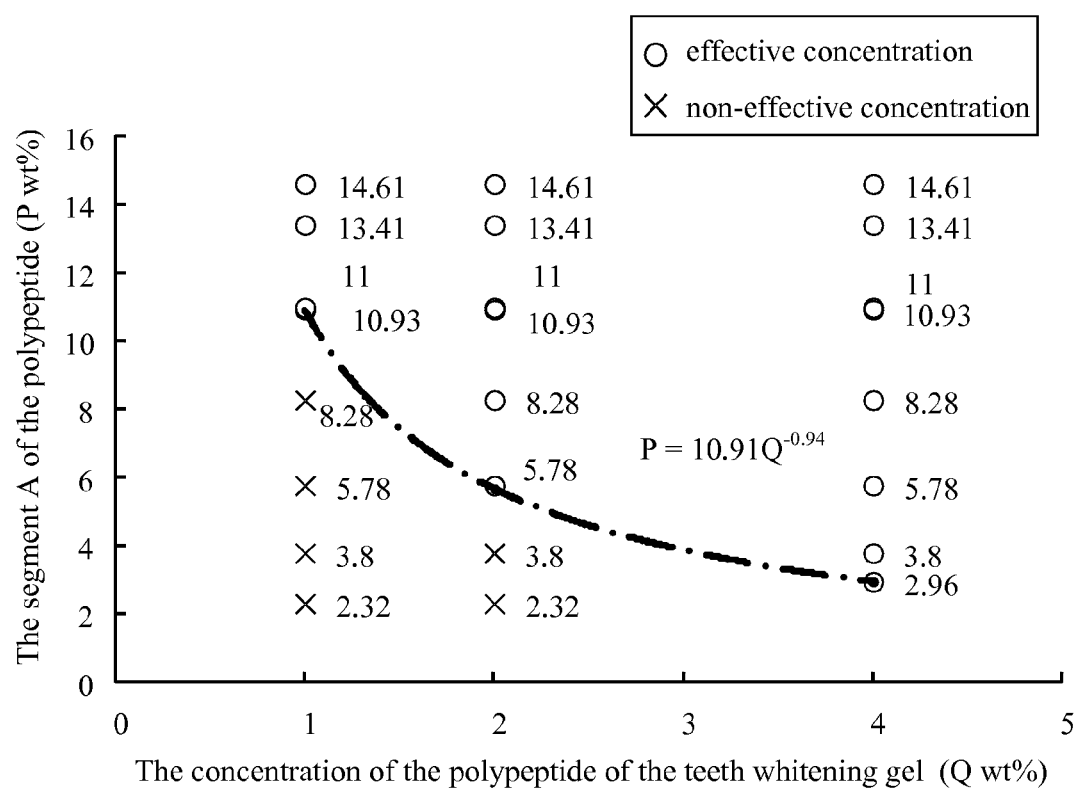

TEETH-WHITENING GEL

RELATED APPLICATIONS

This application claims priority to Taiwan Application Serial Number 101105297, filed Feb. 17, 2012, which is herein incorporated by reference.

BACKGROUND

1. Technical Field

The disclosure relates to a teeth-whitening gel, specifically a high-molecular teeth-whitening gel without thickeners.

2. Description of Related Art

The teeth-whitening is a popular item in cosmetology. The methods of the teeth-whitening can be simply classified into porcelain veneer, all-ceramic crown, and teeth-bleaching, etc. Though the porcelain veneer and the all-ceramic crown are very effective, their acceptability to customers are constantly limited by the disadvantages such as tending to induce sensitive teeth, need of removal of partial healthy teeth, and high cost. In contrast, because the teeth-bleaching has less impact on dental tissues and lower price, and the improvement of techniques and materials, the teeth-bleaching becomes more and more popular these years.

Since the 19th century, scientists had been starting the research in the teeth-bleaching. In the beginning, a bleaching reagent was used to be applied to the surroundings of the teeth. It allows the reagent to permeate the enamel of the teeth for bleaching. However, the efficiency of this method is limited. Next, other scientists had been trying to dispose a bleaching reagent into the pulp cavity directly, and expecting better performance by bleaching the teeth inside out. In 1961, the Spasser's team proposed a method which included mixing sodium perborate and water to form a gel, disposing the gel into the pulp cavity of teeth, and then removing the gel after 1-2 weeks. However, it was inconvenient that the users needed to keep bleaching their teeth by themselves at home for better teeth-bleaching performance. In 1963, the Nutting and Poe's teams proposed an improved method by simply replacing the water used in Spassers's method with a 30% hydrogen peroxide aqueous solution. However, the decomposition of hydrogen peroxide may release free radicals, and an elevated temperature is required to increase the whitening efficiency (U.S. Pat. Nos. 4,528,180 or 4,687,663).

Most bleaching reagents for teeth-whitening were mixtures containing hydrogen peroxide. Now, the main ingredient of a wide variety of the teeth-whitening products is still hydrogen peroxide or its precursors with additional catalysts, surfactants, preservatives or thickeners, etc. For instance, carbamide peroxide, a key ingredient of common teeth-bleaching reagents, is a precursor of hydrogen peroxide. Carbamide peroxide is also named as urea hydrogen peroxide because it will spontaneously decompose into hydrogen peroxide and urea. When the decomposition occurs, the generated urea will increase the pH value and stabilize the generated hydrogen peroxide, and therefore carbamide peroxide is frequently applied in the extended-wear teeth-bleaching at home. However, the teeth-bleaching efficiency of this method is limited because the conversion rate for carbamide peroxide to hydrogen peroxide is not high enough.

From the prior references, many materials other than the aforementioned are used in the teeth-whitening, e.g., hydrochlorites, organic peroxides, inorganic peroxides, hydroperoxides, and peracids, etc. No matter of sodium perborate, hydrogen peroxide or carbamide peroxide, all these peroxides intrinsically possess a certain oxidizing capabilities for the teeth-whitening. However, such whitening ingredients are small molecules of peroxides with high fluidity that would result in allergy or irritation when contacting oral tissues. Thickeners are required as additives in the teeth-whitening ingredients above mentioned to decrease the fluidity and avoid those problems.

The disclosure aims for solving the forgoing shortcomings of relevant prior arts, and provides an efficient solution to enhance safety and convenience of the teeth-whitening operation.

SUMMARY

The disclosure provides a teeth-whitening gel containing a novel polymer. Without an additional thickener, the teeth-whitening gel of the disclosure decreases the fluidity of the gel, and alleviates irritations of the gums and oral tissues.

As an embodiment of the disclosure, the teeth-whitening gel comprises a polypeptide that is contributed to the effective teeth whitening, and water for diluting or dispersing the polypeptide in the gel. The polypeptide is consisting of a segment A and a segment B, wherein the segment A has the following formula (I):

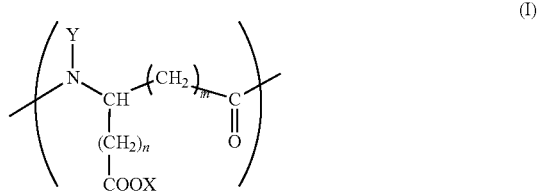

(I)

and the segment B has the following formula (II):

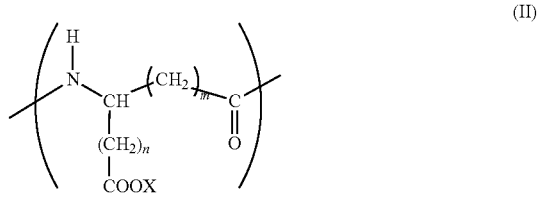

(II)

wherein n is 0 or 1, m is a integer of 0 to 2, and the sum of m and n is not equal to 0; X is H, Na, K, $NH_4$, 1/2 Ca or 1/2 Mg, and Y is Cl, Br or I. The segment A is in a range of 2.96 wt %-15 wt % (as P wt %) of the polypeptide, and the polypeptide is in a range of 1 wt %-4 wt % (as Q wt %) of the teeth-whitening gel, wherein $P \geq 10.91 \times Q^{-0.94}$.

The disclosure also provides a teeth-whitening method. As another embodiment of the disclosure, the teeth-whitening method comprises the steps of cleaning surfaces of a plurality of teeth, and coating the teeth-whitening gel of the disclosure on the surfaces of the cleaned teeth for at least 20 minutes. The teeth-whitening method will effectively whiten the teeth, and alleviate irritations of the gums and oral tissues.

BRIEF DESCRIPTION OF THE DRAWINGS

FIG. 1 is a graph of the concentration of the segment A in the polypeptide and the concentration of the polypeptide of the teeth-whitening gel of the disclosure.

DETAILED DESCRIPTION

For more understanding of the novel teeth-whitening gel provided in the disclosure, several embodiments of the disclosure are enumerated in the followings. However, the embodiments are exemplary and explanatory only, and are not restrictive of the scope and application of the disclosure.

One of the embodiments of the disclosure provides a teeth-whitening gel, wherein the main ingredient is a halogenated polypeptide. The embodiments of the disclosure comprises preparing halogenated polyglutamic acid, detecting the degree of the halogenation of the halogenated polyglutamic acid, and detecting the effect of the teeth-whitening gel containing halogenated polyglutamic acid.

As embodiments, the main ingredients of the teeth-whitening gel are prepared by the chlorination of the polypeptide (such as γ-polyglutamic acid (γ-PGA)), wherein N-H functional groups are chlorinated to generate N—Cl, the halamine group, as a reducing agent. Since the halamine groups are easily decomposed under elevated temperatures and irradiated to release free radicals, redox reactions occur between the halamine groups and the pigments on the surfaces of the teeth. Subsequently the reacted pigments are bleached and removed so as to achieve the teeth-bleaching effect.

In another embodiment of the disclosure, the polypeptide is a polyglutamic acid, which has high hydrophilicity and hygroscopicity. In the food industry, the polyglutamic acid can be used as a thickener or a stabilizer. The polyglutamic acid is also used as a moisturizer in cosmetics and skin care products. Furthermore, since the polyglutamic acid also has high biological compatibility and biodegradability, the polyglutamic acid is eco-friendly. More importantly, the polyglutamic acid has the high stability and safety for human bodies, and does not cause any toxicity, irritation or sensitivity.

The Composition of the Teeth-whitening Gel

According to the teeth-whitening gel provided in the embodiments of the disclosure, the teeth-whitening gel comprises a polypeptide containing halamine group and water for dilution and dispersion of the polypeptide.

The polypeptide is consisting of two segments A and B, wherein the segment A has the following formula (I):

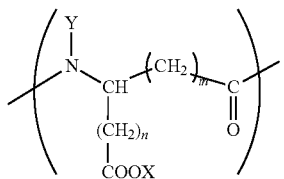

(I)

and the segment B has the following formula (II):

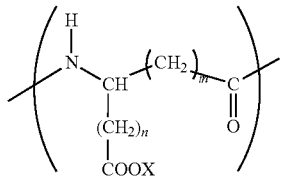

(II)

wherein, n is 0 or 1, m is an integer of 0 to 2, and the sum of m and n is not equal to 0. Otherwise, X is H, Na, K, $NH_4$, 1/2 Ca or 1/2 Mg, and Y is Cl, Br or I.

In the polypeptide, the segment A and the segment B are sequencing randomly. The weight percentage of the segment A of the polypeptide has a preferred weight percentage ranging from 2.96 wt %-15 wt % of the polypeptide, and a more preferred range of 10 wt %-15 wt %. When the weight percentage of the segment A is less than 2 wt % of the polypeptide, the teeth-whitening effect would be poor because of the inadequate halamine concentration. On the other hand, when the weight percentage of the segment A is higher than 15 wt % of the polypeptide, the halogen gas, such as chlorine, would be released with unpleasant smell and cause safety concerns because the halamine concentration in the polypeptide is excessive.

The concentration of the polypeptide in the teeth-whitening gel is in a preferred range of 1 wt %-4 wt %, and a more preferred range of 1 wt %-2 wt %, as preparing the teeth-whitening gel from the foregoing polypeptide. While the concentration of the polypeptide less than 1 wt %, the viscosity of the gel is too low to keep the gel attached on the surface of the teeth to whiten the teeth, and the gel would easily flow in the surrounding tissue of the teeth to cause sensitivity and irritation. On the other hand, while the concentration of the polypeptide higher than 4 wt % of the teeth-whitening gel, the viscosity of the gel is too high to smoothly coat the gel on the surface of the teeth.

According to an embodiment of the disclosure, the segment A of the polypeptide has the following formula:

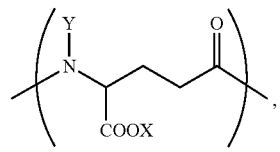

and the segment B has the following formula:

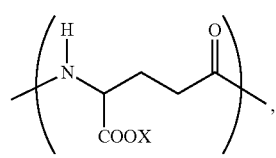

wherein X is H, Na, K, $NH_4$, 1/2 Ca or 1/2 Mg, and preferably is Na. Y is Cl, Br or I, and preferably is Cl.

According to another embodiment of the disclosure, the polypeptide comprises polyglutamic acid, wherein the molecular weight of the polyglutamic acid is preferably lower than or equal to 2,000,000 Dalton (Da), and a more preferred range of 1,000 Da-2,000,000 Da.

And according to another embodiment of the invention, the viscosity of the teeth-whitening gel is 2,000 cps-25,000 cps.

To maintain the whitening effect of the teeth-whitening gel, it is preferred for a certain range of pH value. As an embodiment, the pH value is in a range of 6-8. If the pH value of the teeth-whitening gel is higher than 8, the oxidizing ability of the halamine would be poor, and it results in a decreased reaction rate. It would need longer time to reach the same effect on teeth whitening as that under the pH value of 6-8. And if the pH value is lower than 6, the structure of the polypeptide may be degraded because the acidic condition would cause the cleavage of the peptide bond and decreased molecular weight.

According to an embodiment of the disclosure, a pH buffer can be added into the teeth-whitening gel as an additive if necessary. The pH buffer can prevent the violent change in pH value, which results from the change in concentration of the gel itself, such that the pH value of the gel is controlled in a safe range. According to another embodiment, the pH buffer comprises an aqueous solution of phosphoric acid, sodium bicarbonate, disodium hydrogen phosphate, or the mixture thereof.

The Preparation of the Halogenated Polypeptide and the Teeth-whitening Gel

To prepare the halogenated polypeptide needed on the embodiments of the disclosure, it may use polyglutamic acid and sodium hypochlorite to perform chlorination under room temperature. The buffer solution is phosphoric acid aqueous solution, the pH value of which is adjusted in a range of 6-8. After finishing the chlorination, the product is precipitated by adding appropriate amount of isopropanol. The precipitated product is dried in vacuum after filtrating. Afterwards, a chlorinated polyglutamic acid, i.e. a halogenated polypeptide, according to the embodiments of the disclosure, comes in a powder form with a color of white to light yellow.

The polyglutamic acid for preparing the chlorinated polyglutamic acid is the merchandise of VEDAM corp., and has the molecular weight around 2,000,000 Dalton. In the chlorination, the commercial bleach is applied, wherein sodium hypochlorite as an effective ingredient has a concentration of around 12.65 wt % in the bleach. However, the materials needed on the disclosure are not restricted of the mentioned vendor or any sources.

The teeth-whitening gels in the embodiments of the disclosure are prepared by diluting and dispersing the halogenated polypeptide prepared above into the aqueous solutions of different concentrations.

The Method of Detecting the Concentration of N—Cl Halamine Group of the Polyglutamic Acid The concentration of halamine of chlorinated polyglutamic acid is detected by redox titration with sodium thiosulfate. First, dissolve chlorinated polyglutamic acid in water, and then add potassium iodide as a reducing agent and starch as an indicator in the solution. A few amount of acetic acid can also be added as the catalyst if necessary. The color of the solution is reddish brown at that time. Then, by using the aqueous solution of sodium thiosulfate to titrate the aqueous solution of chlorinated polyglutamic acid, the color of the aqueous solution of the chlorinated polyglutamic acid changes from reddish brown to colorless when meeting the end point of the titration. The volume of the aqueous solution of sodium thiosulfate used is recorded, and then the halamine concentration of the chlorinated polyglutamic acid can be derived.

The method of detecting the concentration of N—Cl group in chlorinated polyglutamic acid is redox titration shown as the following formula (1-1) and (1-2):

$$N\text{—}Cl+2I^-+H^+\rightarrow Cl^-+N\text{—}H+I_2 \quad (1\text{-}1)$$

$$I_2+2S_2O_3^{2-}\rightarrow 2I^-+S_4O_6^{2-} \quad (1\text{-}2)$$

In the following embodiments, the method of detecting the concentration of the N—Cl group of the chlorinated polyglutamic acid comprises the following acts:

1. Prepare an aqueous solution of sodium thiosulfate (Aldrich, US) by adding pure water to dilute to a concentration of 0.025 g/ml.

2. Prepare aqueous solutions of chlorinated polyglutamic acid, wherein the solutions comprise 0.0125 g/ml of chlorinated polyglutamic acid and 0.025 g/ml of potassium iodide, and a few amount of acetic acid as catalyst if necessary.

3. The mixed solutions prepared at act 2 are titrated by the aqueous solution of sodium thiosulfate prepared at act 1, and starch reagent (Aldrich, US) is used as an indicator. It means the end point of the titration is met when the color of the mixed solution changes from reddish brown to colorless. Record the volume of the aqueous solution of sodium thiosulfate used.

According to the titration formula (1-1) and (1-2), calculate the concentration (P wt %) of the segment A having N—Cl group in chlorinated polyglutamic acid by the consumed mole of the aqueous solution of sodium thiosulfate at the end point of titration.

The chemicals used in detecting the content of halamine, such as potassium iodide, sodium thiosulfate and starch, are all from Aldrich.

The Method of Teeth-whitening Using the Teeth-whitening Gel

The embodiment of the disclosure also provides a method of the teeth-whitening, which comprises preparing the teeth-whitening gel, coating it on the teeth surface, and contacting with the teeth's surface for a period of time to gain whitening teeth.

According to the teeth-whitening method provided by the disclosure, the halamine group of the halogenated polyglutamic acid performs redox reaction with the pigments on the teeth's surface to gain whitening teeth. Wherein, N-X groups, in which X may be Cl, Br or I, can be decomposed to form halogen free radicals under heating or irradiation. The halogen free radicals and the pigments on the teeth surface perform redox reaction, and the pigments on the teeth surface would be oxidized, then the color of the teeth's surface would be faded. When the halogen free radicals are released, the original N-X groups may be reduced to be N-H amino groups and form biodegradable polyglutamic acids. The biodegradable polyglutamic acids can be absorbed and digested by human body. Then the generated monomers of glutamic acid can be reused by human bodies or removed through metabolisms. For human body, polyglutamic acids have good biological compatibility, non-toxicity, non-irritation and non-sensitivity. Therefore, the ingredient of the gel with the teeth-whitening effect in the disclosure is safe for human bodies and environment friendly.

The embodiments enumerated below further illustrate the method of the disclosure, but the embodiments are only examples of exemplary and not restricted of the disclosure.

Preparation of the Chlorinated-polyglutamic Acids with Different chlorinated ratio Embodiment 1:

Measure 10.0 g of polyglutamic acid (sodium polyglutamate, the molecular weight of which is around 2,000,000 Dalton, WEDAN, Taiwan) into a 250 ml of single-necked flask, add 90 ml of pure water, and then stir to dissolve completely. Further add 4 g of 12.65 wt % of the aqueous solution of sodium hypochlorite, and then adjust the pH value of the reaction mixture to be 6-8 by adding phosphoric acid aqueous solution (0.5N). Keep stirring the reaction mixture for 30 minutes under room temperature. Transfer the reaction mixture into a separating funnel and precipitate the embodiment 1 by adding 400 ml of isopropanol, and then separate the product by the separating funnel. Then the embodiment 1 is dried under vacuum. The dried embodiment 1 is white to light yellow in a powder form, and can be completely dissolved into water.

Finally, the dried embodiment 1 is titrated by the aqueous solution of sodium thiosulfate, and calculated the concentration of the segment A having N—Cl group in the embodiment (see Table 1).

Embodiment 2~7:

The conditions of experiments are described in the embodiment 1, only the amount of 12.65 wt % of the aqueous solution of sodium hypochlorite is increased from previous 4 to 7.5, 12, 20, 28, 36, and 40 g respectively, added into the reaction mixture. Keep stirring the reaction mixture for 30 minutes under room temperature. Take each set of the reaction mixtures into separating funnels respectively and precipitate the embodiments 2-7 by 400 ml of isopropanol, and separate the products by the separating funnels respectively. Then the embodiments 2-7 are dried under vacuum. The dried embodiments 2-7 are white to light yellow in powder form, and can be completely dissolved into a water solution.

Finally, the dried embodiments 2-7 are respectively titrated by the aqueous solution of sodium thiosulfate, and calculated the concentrations of the segment A having N—Cl group in the embodiments 2-7 (see Table 1).

TABLE 1

| Embodiment (#) | Polyglutamic acid (g) | Aqueous solution of sodium hypochlorite (g) | Reaction time (min) | Concentration of segment A in polyglutamic acid (wt %) |
|---|---|---|---|---|
| 1 | 10 | 4 | 30 | 2.32 |
| 2 | 10 | 7.5 | 30 | 2.96 |
| 3 | 10 | 12 | 30 | 3.80 |
| 4 | 10 | 20 | 30 | 5.78 |
| 5 | 10 | 28 | 30 | 8.28 |
| 6 | 10 | 36 | 30 | 10.93 |
| 7 | 10 | 40 | 30 | 11.0 |

Embodiment 8-9:

The conditions of experiments are described in the embodiment 7 above. Only the reaction times are respectively extended to 90 minutes and 180 minutes. When the two extended reaction times are respectively reached, take each set of the reaction mixtures into separating funnels respectively and precipitate the embodiments 8 and 9 by 400 ml of isopropanol, and separate the products by the separating funnels respectively. Then the embodiments 8 and 9 are dried under vacuum. The dried embodiments 8 and 9 are white to light yellow in powder form, and can be completely dissolved into water.

Finally, the dried embodiments 8 and 9 are respectively titrated by the aqueous solution of sodium thiosulfate, and calculated the concentrations of the segment A having N—Cl group in the Embodiments 8 and 9 (see Table 2).

TABLE 2

| Embodiment (#) | Polyglutamic acid (g) | Aqueous solution of sodium hypochlorite (g) | Reaction time (min) | Concentration of segment A in polyglutamic acid (wt %) |
|---|---|---|---|---|
| 7 | 10 | 40 | 30 | 11.0 |
| 8 | 10 | 40 | 90 | 14.61 |
| 9 | 10 | 40 | 180 | 13.41 |

The Viscosity Measurement and Operation Convenience Test of the Teeth-whitening Gels The viscosity of the teeth-whitening gel provided in this disclosure increases when the concentration of the teeth-whitening gel increases. Since the gel is coated onto the surface of the teeth to whiten the teeth, finding out the optimized viscosity on actual operations is needed. When the concentration of the gel is so low as to having high fluidity, the gel would not be easily attached on the teeth surface. When the concentration of the gel is so high as to having high viscosity, squeezing the gel out of the package during operations would be more difficult and inconvenient. Thus, the disclosure implements the experiments below to form several gels with various concentrations and viscosities. Compare the operation convenience within these gels with different concentrations, and find an optimized concentration of the gel.

In viscosity measurement, measure the gels of the embodiment 1 in different concentrations of the gel respectively by the Brookfield viscometer with needle #5 at 25° C., 50 rpm of centrifuge.

There are subjective and objective ways to evaluate the operation convenience. In subjective way, pack the embodiment 1 in different concentrations of the gel into a 3 ml of injection syringe respectively, and squeeze the syringes by hand. Then give a subjective evaluation on the squeezing difficulties respectively. In objective way, squeeze these gels with different concentrations by a tensile machine in the same squeezing rate (1 cm/min). Then record the quantitative data, squeezing forces, of the gel with different concentrations respectively. The data collected by subjective and objective ways are summarized in Table 3.

TABLE 3

| Polypeptide concentration of gel (wt %) | Viscosity of gel (cps) | Operation convenience | Squeezing force (N) |
|---|---|---|---|
| 0.5 | 583 ± 46 | X | 1.21 ± 0.63 |
| 1.0 | 2153 ± 68 | ○ | 1.76 ± 0.58 |
| 2.0 | 8951 ± 144 | ○ | 2.83 ± 0.42 |
| 4.0 | 24530 ± 183 | Δ | 8.94 ± 0.37 |

[a]subjective evaluation of handling convenience of the gel composites: X is over mobile or hard squeezing, ○ is suitable in use, and Δ needs to squeeze strongly.

Test of the Effect of Teeth-whitening

According to the embodiments of the disclosure, the method of using the teeth-whitening gel to bleach the stained teeth is coating the gel on the surface of the teeth for at least 20 minutes. Not only the contacting time, but also the concentration of the teeth-whitening gel is the key factor to the result of teeth-whitening. In this disclosure, an image analyzer and the CIE color system are applied to evaluate the change of the teeth's color in a quantitative way. The CIE color system is established by the International Commission on Illumination. This system standardizes the photosensitivities of full wavelength of light source to observers in a mathematical equation, and simulates the feeling of human eyes to colors by data (L, a and b) collected by the image analyzer. The mathematical equation is shown as the following equation (2):

$$\Delta E = \sqrt{(\Delta L)^2 + (\Delta a)^2 + (\Delta b)^2} \qquad (2)$$

wherein ΔE is the variation of the color of objects, ΔL is the variation of the brightness of objects, Δa is the chromatic aberration between red and green, and Δb is the chromatic aberration between blue and yellow.

In the following teeth-whiting test, use four sets of teeth in each embodiment. One of the four sets is picked as the control, and the steps described below are performed in each embodiment respectively.

First, the teeth are divided into four sets for different bleaching times (20, 40, 60 minutes, and the control) to be conducted in the second step, and then the respective pictures of the teeth are taken. The control set is not going to be performed the following staining/bleaching steps, and its color is defined as the standard (ΔE is 0). The rest three sets of teeth are stained by immersing them into 0.5 M of Orange II for 24 hours. After 24 hours of staining, pictures are taken on each stained tooth as their backgrounds before they are performed the following bleaching steps.

Second, three different concentrations of the teeth-whitening gels (1, 2, 4 wt %) are prepared for the three sets of the stained teeth mentioned above respectively. One kind of the concentration of the gel is coated on one set of the stained teeth. In each set, the teeth-whitening gels are left attached on the surface of each tooth until reaching three kinds of the reaction times (20, 40, and 60 minutes) respectively.

Finally, pictures are taken and the color changes of the teeth surfaces are recorded. The data (L, a, and b) of each tooth are analyzed and summarized into the tables as shown below.

The color fading (bleaching) ability of the teeth-whitening gels are shown on Table 4-1, Table 5-1 and Table 6-1. The whitening effects of the teeth-whitening gels are shown on Table 4-2, Table 5-2 and Table 6-2.

TABLE 4-2

Whitening effects of 1 wt % of teeth-whitening gel

| Embodiment, # | P wt %[a] | $\triangle\triangle E$[b] | Whitening effect[c] |
|---|---|---|---|
| 1 | 2.32 | 9.4 | X |
| 3 | 3.80 | 9.1 | X |
| 4 | 5.78 | 8.7 | X |
| 5 | 8.28 | 9.5 | X |
| 6 | 10.93 | 17.9 | ○ |
| 7 | 11.0 | 19.7 | ○ |
| 8 | 14.61 | 25.5 | ○ |
| 9 | 13.41 | 25.8 | ○ |

[a] The concentration of segment A in chlorinated polyglutamic acid;
[b] The variation of teeth color after contacting with teeth-whitening gel for 60 min, $\triangle\triangle E = \triangle E(\text{after stained}) - \triangle E(60 \text{ min})$;
[c] X = $\triangle\triangle E < 10$, ○ = $\triangle\triangle E \geq 10$.

TABLE 4-1

Color-fading (bleaching) ability of 1 wt % of teeth-whitening gel

| | L | a | b | ΔE | L | a | b | ΔE |
|---|---|---|---|---|---|---|---|---|
| | Embodiment 1 | | | | Embodiment 3 | | | |
| Control | 80.2 ± 1.2 | −17.2 ± 1.4 | 9.3 ± 1.4 | 0 | 79.4 ± 2.1 | −18.3 ± 1.1 | 8.3 ± 1.2 | 0 |
| After stained | 65.7 ± 3.4 | 7.2 ± 1.3 | 41.2 ± 2.1 | 42.7 | 67.8 ± 1.3 | 7.9 ± 1.2 | 40.4 ± 1.1 | 43.0 |
| 20 min | 68.4 ± 2.1 | 4.4 ± 1.3 | 39.2 ± 1.4 | 38.7 | 68.4 ± 1.2 | 3.2 ± 0.9 | 39.8 ± 1.3 | 39.7 |
| 40 min | 68.1 ± 1.3 | 3.2 ± 2.2 | 38.2 ± 1.2 | 37.4 | 69.3 ± 1.2 | −3.2 ± 1.1 | 38.6 ± 2.2 | 35.3 |
| 60 min | 72.2 ± 2.3 | −3.1 ± 1.2 | 38.4 ± 1.4 | 33.3 | 70.6 ± 1.2 | −3.7 ± 0.9 | 37.6 ± 2.0 | 33.9 |
| | Embodiment 4 | | | | Embodiment 5 | | | |
| Control | 78.9 ± 2.4 | −18.3 ± 1.6 | 8.1 ± 1.0 | 0 | 79.3 ± 2.1 | −18.4 ± 1.1 | 8.2 ± 0.8 | 0 |
| After stained | 65.2 ± 1.4 | 7.1 ± 1.0 | 42.0 ± 1.3 | 44.5 | 66.8 ± 1.2 | 8.3 ± 1.2 | 40.7 ± 1.1 | 43.9 |
| 20 min | 66.2 ± 1.1 | 4.9 ± 1.4 | 40.2 ± 1.4 | 41.6 | 69.1 ± 1.3 | 3.0 ± 0.7 | 39.8 ± 1.4 | 39.5 |
| 40 min | 68.2 ± 1.3 | 3.3 ± 4.2 | 39.2 ± 2.2 | 39.3 | 70.1 ± 1.4 | −2.4 ± 1.3 | 38.6 ± 2.2 | 35.6 |
| 60 min | 69.2 ± 1.4 | −3.3 ± 0.7 | 39.1 ± 1.2 | 35.8 | 70.6 ± 1.5 | −3.9 ± 1.2 | 38.1 ± 1.2 | 34.4 |
| | Embodiment 6 | | | | Embodiment 7 | | | |
| Control | 79.7 ± 1.0 | −17.9 ± 0.7 | 8.5 ± 1.1 | 0 | 79.3 ± 1.3 | −19.9 ± 0.6 | 8.3 ± 0.6 | 0 |
| After stained | 66.4 ± 1.2 | 7.2 ± 0.8 | 41.3 ± 1.1 | 43.4 | 66.3 ± 1.2 | 7.5 ± 0.7 | 40.5 ± 1.2 | 44.2 |
| 20 min | 70.6 ± 1.2 | 4.4 ± 1.2 | 37.3 ± 1.6 | 37.5 | 68.9 ± 1.5 | 4.0 ± 1.4 | 35.2 ± 1.6 | 37.5 |
| 40 min | 72.5 ± 1.3 | −2.1 ± 1.0 | 33.7 ± 1.3 | 30.6 | 71.9 ± 1.1 | −2.7 ± 1.4 | 32.9 ± 1.2 | 30.9 |
| 60 min | 72.8 ± 1.1 | −6.2 ± 1.2 | 28.9 ± 0.8 | 25.5 | 76.1 ± 0.8 | −6.1 ± 2.3 | 29.5 ± 0.8 | 24.5 |
| | Embodiment 8 | | | | Embodiment 9 | | | |
| Control | 80.1 ± 1.3 | −17.8 ± 1.1 | 8.6 ± 0.9 | 0 | 79.8 ± 1.3 | −18.5 ± 1.0 | 8.7 ± 1.0 | 0 |
| After stained | 67.6 ± 1.2 | 7.7 ± 0.8 | 39.1 ± 1.0 | 41.7 | 67.6 ± 1.2 | 7.9 ± 0.5 | 39.1 ± 1.1 | 42.1 |
| 20 min | 70.6 ± 0.9 | 4.1 ± 0.6 | 32.5 ± 0.7 | 33.8 | 69.4 ± 1.0 | 4.0 ± 0.8 | 32.1 ± 0.8 | 34.1 |
| 40 min | 72.9 ± 1.1 | −3.2 ± 0.8 | 24.2 ± 1.2 | 22.5 | 72.3 ± 1.1 | −3.1 ± 0.9 | 24.1 ± 1.2 | 23.0 |
| 60 min | 75.2 ± 1.1 | −5.5 ± 1.1 | 17.9 ± 1.3 | 16.2 | 75.2 ± 1.0 | −5.2 ± 2.1 | 16.9 ± 1.3 | 16.3 |

TABLE 5-1

Color-fading (bleaching) ability of 2 wt % of teeth-whitening gel

| | L | a | b | $\triangle E$ | L | a | b | $\triangle E$ |
|---|---|---|---|---|---|---|---|---|
| | Embodiment 1 | | | | Embodiment 3 | | | |
| Control | 78.9 ± 2.1 | −18.4 ± 1.4 | 8.5 ± 1.6 | 0 | 80.2 ± 2.3 | −17.7 ± 0.2 | 8.3 ± 0.8 | 0 |
| After stained | 65.7 ± 3.4 | 7.2 ± 1.3 | 41.2 ± 2.1 | 43.6 | 66.7 ± 1.6 | 8.1 ± 1.1 | 40.4 ± 1.3 | 42.6 |
| 20 min | 67.4 ± 2.1 | 4.9 ± 1.4 | 40.2 ± 1.4 | 41.2 | 68.2 ± 2.3 | 3.1 ± 0.7 | 39.3 ± 1.6 | 38.8 |
| 40 min | 68.1 ± 3.3 | 3.3 ± 4.2 | 39.2 ± 2.2 | 40.0 | 69.7 ± 1.7 | −2.2 ± 1.4 | 38.5 ± 3.2 | 35.0 |
| 60 min | 70.2 ± 2.5 | −3.1 ± 1.1 | 39.4 ± 1.5 | 34.7 | 70.6 ± 1.5 | −3.8 ± 1.1 | 37.6 ± 2.1 | 34.3 |
| | Embodiment 4 | | | | Embodiment 5 | | | |
| Control | 79.3 ± 1.2 | −18.1 ± 0.7 | 8.6 ± 1.4 | 0 | 80.4 ± 2.3 | −18.3 ± 1.1 | 8.8 ± 1.2 | 0 |
| After stained | 66.3 ± 2.2 | 7.4 ± 1.1 | 40.3 ± 2.1 | 41.9 | 67.3 ± 1.6 | 7.8 ± 1.5 | 39.6 ± 1.3 | 41.2 |
| 20 min | 70.3 ± 2.1 | 4.1 ± 2.4 | 37.5 ± 2.1 | 36.7 | 70.4 ± 1.1 | 4.0 ± 1.2 | 32.1 ± 0.8 | 33.3 |
| 40 min | 72.2 ± 1.2 | −2.8 ± 1.3 | 33.2 ± 1.6 | 29.0 | 73.3 ± 2.1 | −3.3 ± 0.9 | 24.3 ± 2.2 | 22.3 |
| 60 min | 76.3 ± 1.4 | −6.3 ± 2.2 | 29.8 ± 1.2 | 24.4 | 76.2 ± 1.1 | −5.4 ± 3.1 | 17.4 ± 2.3 | 15.8 |
| | Embodiment 6 | | | | Embodiment 7 | | | |
| Control | 79.3 ± 0.8 | −18.4 ± 3.1 | 8.3 ± 1.7 | 0 | 79.8 ± 1.4 | −18.6 ± 2.6 | 7.9 ± 1.1 | 0 |
| After stained | 66.8 ± 3.4 | 7.2 ± 2.1 | 42.2 ± 2.3 | 43.9 | 65.4 ± 2.3 | 7.3 ± 2.4 | 42.4 ± 1.2 | 45.4 |
| 20 min | 70.2 ± 2.1 | 0.2 ± 1.0 | 36.4 ± 1.0 | 34.5 | 71.1 ± 2.0 | −1.1 ± 0.8 | 33.1 ± 1.4 | 32.1 |
| 40 min | 74.2 ± 1.7 | −6.4 ± 1.5 | 23.2 ± 1.1 | 19.8 | 76.2 ± 1.6 | −5.2 ± 1.4 | 25.3 ± 2.1 | 21.8 |
| 60 min | 76.8 ± 1.2 | −10.1 ± 1.7 | 18.2 ± 2.5 | 13.0 | 79.6 ± 2.1 | −9.6 ± 1.2 | 18.1 ± 1.1 | 13.5 |
| | Embodiment 8 | | | | Embodiment 9 | | | |
| Control | 81.0 ± 0.9 | −18.5 ± 1.2 | 8.8 ± 1.7 | 0 | 80.6 ± 1.2 | −17.8 ± 1.3 | 8.4 ± 1.8 | 0 |
| After stained | 66.1 ± 2.4 | 7.6 ± 2.3 | 45.2 ± 1.4 | 40.3 | 66.4 ± 3.1 | 7.2 ± 1.2 | 44.7 ± 1.7 | 47.1 |
| 20 min | 71.7 ± 1.3 | −2.1 ± 0.9 | 32.1 ± 2.2 | 29.7 | 72.3 ± 1.1 | −2.5 ± 1.0 | 33.4 ± 1.4 | 31.0 |
| 40 min | 79.2 ± 1.5 | −5.3 ± 1.1 | 23.7 ± 2.9 | 20.6 | 78.5 ± 1.4 | −6.3 ± 1.5 | 21.3 ± 2.3 | 17.8 |
| 60 min | 80.2 ± 1.1 | −13.2 ± 1.4 | 13.2 ± 1.7 | 7.3 | 79.1 ± 2.1 | −14 ± 1.1 | 17.4 ± 2.5 | 10.0 |

TABLE 5-2

Whitening effects of 2 wt % of teeth-whitening gel

| Embodiment, # | P wt %[a] | $\triangle\triangle E$[b] | Whitening effect[c] |
|---|---|---|---|
| 1 | 2.32 | 8.9 | X |
| 3 | 3.80 | 8.3 | X |
| 4 | 5.78 | 17.5 | ◯ |
| 5 | 8.28 | 25.4 | ◯ |
| 6 | 10.93 | 30.9 | ◯ |
| 7 | 11.0 | 31.9 | ◯ |
| 8 | 14.61 | 33.0 | ◯ |
| 9 | 13.41 | 37.1 | ◯ |

[a]The concentration of segment A in chlorinated polyglutamic acid;
[b]The variation of teeth color after contacting with teeth-whitening gel for 60 min, $\triangle\triangle E = \triangle E$(after stained) − $\triangle E$(60 min);
[c]X = $\triangle\triangle E$ < 10, ◯ = $\triangle\triangle E$ ≥ 10.

TABLE 6-1

Color-fading (bleaching) ability of 4 wt % of teeth-whitening gel

| | L | a | b | $\triangle E$ | L | a | b | $\triangle E$ |
|---|---|---|---|---|---|---|---|---|
| | Embodiment 2 | | | | Embodiment 3 | | | |
| Control | 79.8 ± 1.0 | −18.6 ± 0.8 | 8.4 ± 1.6 | 0 | 80.2 ± 1.3 | −17.9 ± 1.3 | 8.9 ± 0.6 | 0 |
| After stained | 65.8 ± 1.2 | 7.3 ± 1.3 | 40.8 ± 1.9 | 43.8 | 66.4 ± 1.1 | 8.1 ± 1.0 | 39.2 ± 1.3 | 42.2 |
| 20 min | 68.3 ± 1.1 | 4.0 ± 0.4 | 37.1 ± 1.1 | 38.3 | 70.7 ± 1.2 | 5.0 ± 1.2 | 35.1 ± 0.6 | 36.1 |
| 40 min | 71.2 ± 0.8 | −2.7 ± 0.3 | 35.2 ± 1.1 | 32.3 | 73.8 ± 1.3 | −3.5 ± 0.5 | 29.3 ± 1.2 | 25.8 |
| 60 min | 74.3 ± 1.2 | −6.2 ± 1.2 | 31.8 ± 1.3 | 24.0 | 76.1 ± 1.2 | −5.5 ± 1.3 | 25.4 ± 1.3 | 21.0 |
| | Embodiment 4 | | | | Embodiment 5 | | | |
| Control | 79.9 ± 1.2 | −18.2 ± 1.8 | 7.9 ± 1.1 | 0 | 80.6 ± 1.2 | −18.8 ± 1.0 | 8.1 ± 1.3 | 0 |
| After stained | 64.4 ± 1.3 | 7.5 ± 2.0 | 41.4 ± 1.0 | 45.0 | 65.4 ± 2.1 | 8.3 ± 1.1 | 44.6 ± 1.4 | 47.9 |
| 20 min | 69.1 ± 1.0 | −0.1 ± 0.5 | 34.1 ± 1.4 | 33.6 | 73.3 ± 0.7 | −0.5 ± 0.7 | 36.4 ± 1.2 | 34.5 |
| 40 min | 73.2 ± 1.6 | −5.6 ± 1.1 | 25.3 ± 1.1 | 22.5 | 77.5 ± 1.1 | −6.6 ± 0.5 | 25.3 ± 1.3 | 21.3 |
| 60 min | 78.6 ± 2.1 | −9.7 ± 1.0 | 19.1 ± 0.5 | 14.1 | 79.0 ± 1.1 | −14.8 ± 1.0 | 18.4 ± 1.5 | 11.2 |

TABLE 6-1-continued

Color-fading (bleaching) ability of 4 wt % of teeth-whitening gel

| | L | a | b | ΔE | L | a | b | ΔE |
|---|---|---|---|---|---|---|---|---|
| | Embodiment 6 | | | | Embodiment 7 | | | |
| Control | 81.6 ± 0.2 | −18.8 ± 1.7 | 8.2 ± 1.0 | 0 | 80.6 ± 1.2 | −18.8 ± 1.3 | 8.2 ± 0.8 | 0 |
| After stained | 65.4 ± 1.1 | 7.2 ± 1.2 | 44.7 ± 1.3 | 47.3 | 65.4 ± 1.1 | 7.1 ± 0.5 | 44.1 ± 1.1 | 46.8 |
| 20 min | 72.3 ± 1.1 | −1.5 ± 0.8 | 34.4 ± 1.0 | 32.7 | 72.1 ± 1.1 | −2.8 ± 1.0 | 34.4 ± 1.4 | 31.9 |
| 40 min | 77.5 ± 1.6 | −6.3 ± 1.1 | 22.3 ± 1.3 | 19.3 | 77.8 ± 1.0 | −6.9 ± 1.5 | 21.6 ± 1.3 | 18.1 |
| 60 min | 79.5 ± 1.1 | −14.7 ± 1.0 | 17.1 ± 1.5 | 10.0 | 79.6 ± 0.6 | −14.1 ± 1.1 | 17.1 ± 1.2 | 10.1 |
| | Embodiment 8 | | | | Embodiment 9 | | | |
| Control | 81.6 ± 0.8 | −18.3 ± 1.0 | 8.2 ± 1.0 | 0 | 81.6 ± 1.2 | −18.8 ± 1.2 | 8.7 ± 1.1 | 0 |
| After stained | 65.4 ± 1.2 | 7.3 ± 1.7 | 44.7 ± 1.3 | 47.4 | 65.4 ± 2.1 | 8.2 ± 1.0 | 44.1 ± 1.1 | 47.4 |
| 20 min | 72.3 ± 1.1 | −1.5 ± 1.1 | 34.4 ± 1.1 | 32.5 | 71.3 ± 1.3 | −1.5 ± 1.1 | 33.8 ± 1.2 | 32.2 |
| 40 min | 78.7 ± 1.0 | −6.6 ± 1.2 | 22.1 ± 1.3 | 18.4 | 77.8 ± 1.5 | −6.7 ± 1.2 | 22.3 ± 1.3 | 18.6 |
| 60 min | 79.8 ± 1.5 | −13.9 ± 1.2 | 16.4 ± 1.5 | 9.5 | 79.3 ± 1.4 | −14.2 ± 1.0 | 16.4 ± 1.1 | 9.3 |

TABLE 6-2

Whitening effects of 4 wt % of teeth-whitening gel

| Embodiment, # | P wt %[a] | ΔΔE[b] | Whitening effect[c] |
|---|---|---|---|
| 2 | 2.96 | 19.8 | ○ |
| 3 | 3.80 | 21.2 | ○ |
| 4 | 5.78 | 30.9 | ○ |
| 5 | 8.28 | 36.7 | ○ |
| 6 | 10.93 | 37.3 | ○ |
| 7 | 11.0 | 36.7 | ○ |
| 8 | 14.61 | 37.9 | ○ |
| 9 | 13.41 | 38.1 | ○ |

[a]The concentration of segment A in chlorinated polyglutamic acid;
[b]The variation of teeth color after contacting with teeth-whitening gel for 60 min, ΔΔE = ΔE(after stained) − ΔE(60 min);
[c]X = ΔΔE < 10, ○ = ΔΔE ≥ 10.

According Table 4-1, Table 5-1 and Table 6-1, the teeth-whitening effect of the gel is enhanced if the degree of the chlorination in polyglutamic acid is increased; when the time of contacting (the teeth-whitening gel to the tooth's surface) is longer, the ΔE of the stained teeth becomes even closer to the ΔE of the control. It confirms that the variables, the concentration of reactant (chlorinated polyglutamic) and the contacting (reaction) time, are positive correlated to the teeth-whitening effect of the teeth-whitening gel. The reason is that both the higher degree of the chlorination in polyglutamic acid and longer contacting time are positive for redox reactions to reach a higher extent of reaction. The more pigments on the teeth are oxidized, the whiter the teeth become.

ΔΔE is defined as the color variation between the color of the stained teeth and the teeth contacted by the teeth-whitening gel for 60 mins (ΔΔE=ΔE (after stained)−ΔE (60 min)) in each embodiment. The ΔΔE values and the concentrations of segment A in chlorinated polyglutamic acid (P wt %) of all embodiments are listed in Table 4-2, Table 5-2 and Table 6-2. Further the minimum value of ΔΔE is given as 10 while judging the teeth-whitening effect is obvious.

In Table 4-2 (the concentration of the gel is 1 wt %), each of the embodiment 1, 3-5 with lower P % (2.32-8.28 wt %) has the value of ΔΔE less than 10, which means the teeth-whitening effect is not significant. However, when P % increases to 10.93% or above, as that in the embodiments 6-9, the value of ΔΔE also increases to 17.9 or above. It represents that the significant teeth-whitening effect has been achieved while the P % is above 10.93%. According to this way of data analysis, conclude 10.93% is the minimum value of P % under the concentration of the teeth-whitening gel (Q %) is 1%.

Similarly, from the data in Table 5-2, Table 6-2, the P % with the value of ΔΔE above 10 is selected. the minimum values of P % are concluded as 5.78% (ΔΔE being 17.5), 10.93% (ΔΔE being 17.9) under the concentration of the teeth-whitening gel (Q %) of 2%, and 4%, respectively. Those values of P % are the minimum effective concentrations of segment A in chlorinated polyglutamic acid under different concentrations of the teeth-whitening gels (1, 2, 4%), and the boundary conditions of two variables, the concentration of segment A in chlorinated polyglutamic acid (P %)/the concentrations of the teeth-whitening gels (Q %), are determined. The summary is shown in Table 7, and Q is related to P in a mathematical equation below:

$$P \geq 10.91 \times Q^{-.94}, \text{ wherein } P\% \geq 2.96\%$$

TABLE 7

| Concentration of teeth-whitening gel (Q wt %) | Minimum effective concentration of segment A in chlorinated polyglutamic acid (P wt %) |
|---|---|
| 1 | 10.93 |
| 2 | 5.78 |
| 4 | 2.96 |

According to Table 7 and FIG. 1, when the concentration on teeth-whitening gel is decreased, the minimum effective concentration of segment A in chlorinated polyglutamic acid (P %) needs to be higher so as to achieve significant teeth-whitening effect. However, if the concentration of segment A in chlorinated polyglutamic acid (P %) is higher than 15 wt %, the concentration of halamine contained in chlorinated polyglutamic acid is excessive, and generates chlorine gas or release a large amount of chloride ion to cause the damage to the human body. Therefore, the concentration of segment A in chlorinated polyglutamic acid (P %) is preferably maintained in a range of 2.96 wt %-15 wt %.

Further, the polyglutamic acid used in the embodiments of the disclosure is a natural fermented product, which has the even higher biocompatibility and biodegradability. Therefore, it does no harm to environment, and more importantly, has no healthy and safety concerns, e.g., toxicity, irritation or allergy, to human beings. The teeth-whitening gels of the disclosure not only have properties as trustful as naturally made, but also the good oxidation feature of the halamine to effectively achieve the teeth-whitening effect.

What is claimed is:

1. A teeth-whitening gel comprising:
   water; and
   a tooth-whitening effective amount of a polypeptide consisting of a segment A and a segment B;
   the segment A having the following formula:

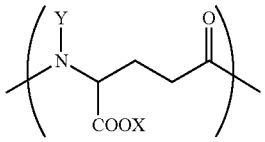

the segment B having the following formula:

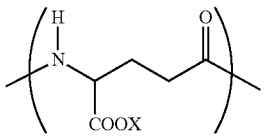

wherein X is H, Na, K, $NH_4$, 1/2 Ca or 1/2 Mg, Y is Cl, Br or I, and
   wherein the segment A is in a range of 2.96 wt %-15 wt % of the polypeptide (as P wt %), and the polypeptide is in a range of 1 wt %-4 wt % of the teeth-whitening gel (as Q wt %), wherein $P \geq 10.91 \times Q^{-0.94}$.

2. The teeth-whitening gel of claim 1, wherein the polypeptide has a molecular weight equal to or less than 2,000,000 Dalton.

3. The teeth-whitening gel of claim 1, wherein the teeth-whitening gel has a viscosity equal to or more than 2,000 cps.

4. The teeth-whitening gel of claim 1, wherein the teeth-whitening gel has a pH value between 6 and 8.

5. The teeth-whitening gel of claim 4, wherein the teeth-whitening gel further comprises a pH buffer agent.

6. The teeth-whitening gel of claim 5, wherein the pH buffer agent is an aqueous solution of phosphoric acid, sodium bicarbonate, disodium hydrogen phosphate, or a mixture thereof.

7. A teeth-whitening method, comprising:
   cleaning surfaces of a plurality of teeth; and
   coating the teeth-whitening gel described in claim 1 over the cleaned surfaces of the teeth, wherein the contacting time is at least 20 minutes.

8. The teeth-whitening method of claim 7, wherein the contacting time is at least 60 minutes.

* * * * *